United States Patent [19]

Busch et al.

[11] Patent Number: 4,794,077
[45] Date of Patent: Dec. 27, 1988

[54] DETECTION OF HUMAN CANCER CELLS WITH ANITBODIES TO HUMAN CANCER NUCLEOLAR ANTIGEN P145

[75] Inventors: Harris Busch; James W. Freeman; Rose K. Busch, all of Houston, Tex.

[73] Assignee: Biosciences Corporation of Texas, Houston, Tex.

[21] Appl. No.: 808,913

[22] Filed: Dec. 13, 1985

[51] Int. Cl.$^4$ ................. G01N 33/53; C12N 5/00; C07K 3/20

[52] U.S. Cl. ................. 435/7; 424/106; 435/172.2; 435/240.27; 436/503; 436/508; 436/548; 436/813; 530/413; 530/417; 530/387; 935/108; 935/110

[58] Field of Search ............. 436/548, 813, 508, 518, 436/503, 808, 543; 424/9, 106; 530/828, 846, 809, 412, 387, 413, 416, 417; 435/810, 7, 240, 27, 172.2; 935/108, 110

[56] References Cited

U.S. PATENT DOCUMENTS 4,448,890  5/1984  Smetana et al. ............. 436/508
4,725,669  2/1988  Essex et al. ............. 530/322

OTHER PUBLICATIONS

Kohler et al., Nature, vol. 256, Aug. 7, 1975, pp. 495-497.
Davis et al., Journal of Immunological Methods, vol. 58, 1983, pp. 349-357.
Davis et al., Proc. Natl. Acad. Sci., U.S.A., vol. 76, No. 2, 1979, pp. 892-896.
Lu M. et al., AM J Pathol; 123(1):73-8 (Apr. 1986).
Miyawaki S., et al., Arthritis Rheum; 19(6):726-36 (1973).
Davis F. M. et al., Blood; 63(3):676-83 (1984).
Ford R. J. et al., Blood; 63(3):559-65 (1984).
Smetana K., et al., Blut; 46(3):133-41 (1983).
Satoh K., et al., Cancer Res; 43(5):2143-9 (1983).
Chan, P. K., et al., Cancer Res; 40(9):3194-201 (1980).
Reiners J. J. Jr., et al., Cancer Res; 40(5):1367-71 (1980).
Busch, H., et al., Cancer Res; 39(8):3024-30 (1979).
Marashi, F., et al. Cancer Res; 39(1):59-66 (1979).
Davis, F. M., et al., Cancer Res; 38(7):1906-15 (1978).
Chatterjee, A., et al., Cancer Res; 47(4):1123-9 (Feb. 1987).
Freeman, J. W., et al., Cancer Res; 47(2):586-91 (Jan. 1987).
Freeman, J. W., et al., Cancer Res; 46(7):3593-8 (Jul. 1986).
Freeman, J. W., et al., Cancer Res; 45(11 Pt 2):5637-42 (Nov. 1985).
Baak, J. P., Histopathology; 9(4):437-44 (Apr. 1985).
Hashimoto C., et al., J. Biol. Chem.; 258(3):1379-82 (1983).
Lischwe M. A., et al., J. Biol. Chem; 260(26):14304-10 (Nov. 1985).
Busch R. K., et al., Proc. Soc. Exp. Biol. Med.; 168(1):125-30 (1981).
Rusch H., et al., Adv. Exp. Med. Biol.; 92:125-80 (1977).
Love R., et al., Ann. Clin. Lab. Sci.; 4(3):131-8 (1974).
Mamaev N. N., et al., Biull. Eksp. Biol. Med.; 99(4):477-9 (Apr. 1985) (Published in Russian).
Busch H., et al., Cancer Invest.; 1(1):24-40 (1983).
Spohn W. H., et al., Cancer Invest.; 3(4):307-20 (1985).
Kelsey D. E., et al., Cancer Lett.; 12(4):295-303 (1981).
Busch H., et al., Cardiovasc. Res. Cent. Bull.; 19(3):61-99 (1981).
Todorov I. T., et al., Cell. Biol. Int. Rep.; 11(3):181-7 (Mar. 1987).
Busch H., et al., Cell Biophys.; 2(4):315-25 (1980).
Busch H., et al., Clin. Immunol Immunopathol.; 18(2):155-67 (1981).
Trent J. M., et al., Cytogenet. Cell Genet.; 30(1):31-8 (1981).
Steele R. E., et al., Dev. Biol.; 102(2):409-16 (1984).
Kamata T., et al., Int. J. Cancer; 34(5):657-65 (1984).
Reichlin M., et al., J. Clin. Immunol.; 4(1):40-4 (1984).
Pazourek J., Neoplasma; 26(2):201-4 (1979).
Busch H., et al., Prog. Clin. Biol. Res.; 132E:229-46 (1983).
Gyorkey F., Prog. Clin. Biol. Res.; 75A:491-502 (1981).
Chan P. K., et al., Transplant Proc.; 13(4):1955-7 (1981).
Busch H. et al., Transplant Proc.; 12(1):99-102 (1980).
Tannenbaum M., et al., Urology; 19(5):546-51 (1982).
American Journal of Pathology, "A Selected Bibliography with Abstracts Pertaining to Nucleolar Antigens".
Freeman et al., Cancer Research 45:5637 (1985), "Masking of Nontumorous Antigens for Development of Human Tumor Nucleolar Antibodies with Improved Specificity".

Primary Examiner—Robert J. Warden
Assistant Examiner—Florina B. Hoffer
Attorney, Agent, or Firm—Arnold, White & Durkee

[57] ABSTRACT

Specific common nucleolar antigens are found in a broad range of human malignant tumor specimens and have been isolated, extracted and purifed. Monoclonal antibodies specific to one of these nucleolar antigens (p145) are harvested from mouse ascites or culture supernatant and used for detection of human cancer cells. Disclosed are (1) methods of isolating the nucleolar antigen, obtaining the antigen in substantially purifed form, producing the specific antibodies, obtaining them in substantially purified form, and using the antibodies induced by the nucleolar antigen in diagnostic procedures for detecting human cancer cells, and (2) diagnostic kits comprising specific antibodies.

16 Claims, No Drawings

DETECTION OF HUMAN CANCER CELLS WITH ANITBODIES TO HUMAN CANCER NUCLEOLAR ANTIGEN P145

The Government may have rights in this invention subject to funding grants provided by the Department of Health and Human Services No. 5 PO1-CA-10893-19.

FIELD OF THE INVENTION

This invention relates to nucleolar antigen p145 found in a broad range of human cancers and not found in corresponding non-tumor tissues and to antibodies and antisera specific to this nucleolar antigen for diagnostic purposes.

BACKGROUND OF THE INVENTION

Earlier findings in experimental animals have indicated the presence of nuclear and nucleolar antigens in tumors which were not found in non-tumor tissues (R. K. Busch et al, Cancer Res. 34, 2362, 1974; Yeoman et al, Proc. Natl. Acad. Sci. US 73, 3258, 1976; Busch and Busch, Tumori 63, 347, 1977; Davis et al, Cancer Res. 38, 1906, 1978; Marashi et al, Cancer Res. 39, 59, 1979). In these early studies by the inventors, antibodies were prepared to nucleoli of rat normal and neoplastic cells by immunization of rabbits (R. K. Busch et al, supra; Busch and Busch, supra; Davis et al, supra). Bright nucleolar fluorescence was demonstrated in the acetone-fixed tumor cells by the indirect immunofluorescence method. It was also found that the immunoprecipitin bands in Ouchterlony gels formed with antisera to Novikoff hepatoma nucleolar antigens extracted from rat Novikoff hepatoma nucleoli differed from the corresponding immunoprecipitin bands produced with liver nucleolar antigens and antiliver nucleolar antisera (Busch and Busch, supra).

Further specificity was shown when antitumor nucleolar antiserum absorbed with liver nuclear extracts produced positive nucleolar fluorescence in Novikoff hepatoma ascites cells but not in liver cells. Conversely, antiliver nucleolar antiserum absorbed with tumor nucleolar extracts did not produce detectable tumor nucleolar fluorescence but did produce positive fluorescence in liver nucleoli (Davis et al, supra).

Inasmuch as immunofluorescence analysis indicated that differences were observable in acetone-fixed tumor smears and normal rat cell smears (particularly after absorption of the antisera with normal liver nuclei and nucleoli), attempts were made to utilize these antisera to rat tumor nucleolar antigens in testing corresponding tissue samples derived from human tumors. Studies with antibodies to rodent tumor nucleoli showed that positive immunofluorescence was not found in human tumor nucleoli. In view of this, the present inventors began a new series of experiments to find specific human nucleolar antigens. Positive immunofluorescence was then found in human tumor tissues with antisera and antibodies to these new human tumor nucleolar preparations. In these studies, the antibodies were absorbed with placental nuclear sonicates as well as fetal calf serum (Busch et al, 39, 3024, 1979; Davis et al, Proc. Natl. Acad. Sci. USA 76, 892, 1979; Smetana et al, Life Sci. 25, 227, 1979).

The present invention has resulted from studies designed to produce monoclonal antibodies to specific human tumor nucleolar antigens. The advantage of monoclonal antibodies over polyclonal antibodies is that monoclonal antibodies are highly specific and they can be harvested in an unlimited supply. Such monoclonal antibodies have now been developed to a human tumor nucleolar antigen (p145).

The nucleolar antigen (p145) has a molecular size of 145 kD and has been shown by immunoelectromicroscopy to be localized within fibrillar centers and granular region of the nucleous of tumor cells. Monoclonal antibodies to the nucleolar antigen p145 have been used in immunofluorescence and/or immunoperoxidose methods for determining the expression of this antigen in various pathologic and normal human tissues.

The following Table I presents a summary of the human cancers in which bright nucleolar immunofluorescence was found with monoclonal antibodies to nucleolar antigen p145. These studies support the previous studies using polyclonal antisera that human tumors contain common nucleolar antigen(s) that can be detected with specific antibodies.

In the non-tumor tissues, benign tumors, and inflammation states, negative results were generally obtained as indicated in the following Table II.

These results, originally obtained with immunofluorescence, have been verified and extended with immunoperoxidase methods.

BACKGROUND REFERENCES

Busch, H., Gyorkey, F., Busch, R. K., Davis, F. M., Gyorkey, P. and Smetana, K. A. nucleolar antigen found in a broad range of human malignant tumor specimens. Cancer Res. 39: 3024–3030, 1979.

Busch, R. K. and Busch, H. Antigenic proteins of nucleolar chromatin of NOvikoff hepatoma ascites cells. Tumori 63: 347–357, 1977.

Busch, R. K., Daskal, I., Spohn, W. H., Kellermayer, M. and Busch, H. Rabbit antibodies to nucleoli of Novikoff hepatoma and normal liver of the rat. Cancer Res. 34: 2362–2367, 1974.

Bruck, C., Portelle, D. Glinear, C. and Bullen, A. One step purification of mouse monoclonal antibodies from ascites fluid by DEAE affi-gel blue chromatography. J. Immunol. Meth. 53: 313–319, 1982.

Dale, G. and Latner, S. L. Isoelectric focusing of serum proteins in acrylamide gels followed by electrophoresis. Clin. Chim. Acta 24: 61–68, 1969.

Davis, F. M., Busch R. K., Yeoman, L. C. and Busch, H. Differences in nucleolar antigens of rat liver and Novikoff hepatoma ascites cells. Cancer Res. 38: 1906–1915, 1978.

Davis, F. M., Gyorkey, F., Busch, R. K. and Busch, H. A. nucleolar antigen found in several human tumors but not in nontumor tissues studied. Proc. Natl. Acad. Sci. USA 7s6: 892–896, 1979.

Garvey, J. S., Cremer, N. E., and Sussdorf, D. H. Methods in Immunology, 1977. W. A. Benjamin, Inc. Reading, Mass.

Hilgers, J., Nowinski, R. C., Geering, G. and Hardy, W. Detection of avian and mmalian oncogenic RNA viruses (oncornaviruses) by immunofluorescence. Cancer Res. 32: 98–106, 1972.

Kendall, F. E. The use of immunochemical methods for the identification and determination of human serum proteins. Cold Spring Harbor Symp. Quant. Biol. 6: 376–384, 1938.

Laurell, C. B. Electroimmunoassay. Scand. J. Clin. Lab. Invest. 29 (Suppl. 124): 21–37, 1972.

Lowry, O. H., Rosebrough, N. J., Farr, A. L. and Randall, R. J. Protein measurement with the Folin phenol reagent. J. Biol. Chem. 193: 265-275, 1951.

Marashi, F., Davis, F. M., Busch, R. K., Savage, H. E. and Busch, H. Purification and partial characterization of nucleolar antigen-1 of the Novikoff hepatoma. Cancer Res. 39: 59-66, 1979.

Smetana, K., Busch, R. K., Hermansky, F. and Busch, H. Nucleolar immunofluorescence in human hematological malignancies. Life Sci. 25: 227-234, 1979.

Tan, E. M. and Lerner, R. A. An immunological study of the fate of nuclear and nucleolar macromolecules during the cell cycle. J. Mol. Biol. 68: 107-114, 1972.

Wallace, R. W., Yu, P. H., Dieckert, J. P. and Dieckert, J. W. Visualization of protein-SDS complexes in polyacrylamide gels by chilling. Anal. Biochem. 61: 86-92, 1974.

Yeoman, L. C., Jordan, J. J., Busch, R. K., Taylor, C. W., Savage,, H. and Busch, H. A fetal protein in the chromatin of Novikoff hepatoma and Walker 256 carcinosarcoma tumors that is absent from normal and regenerating rat liver. Proc. Natl. Acad. Sci. USA 73: 3258-3262, 1976.

SUMMARY OF THE INVENTION

The present invention resides in the surprising and unexpected discovery that a common nucleolar antigen (p145), having a molecular weight of about 140 Kd to about 150 Kd, is found in a broad range of human cancer cells but is not found in normal human cells. The antigen is a protein which may have gene control or other functions andd is persistent throughout mitosis in a perichromosomal location. Important aspects of the invention are discovery of a common nucleolar antigen found in human cancer cells, isolation and purification of this nucleolar antigen, production of monoclonal antibodies specific to this antigen, diagnostic test methods using monoclonal antibodies specific to this antigen to detect human cancerr cells, a diagnostic kit containing monoclonal antibodies specific to the nucleolar antigen p145.

Accordingly, an object of the present invention is the provision of the common nucleolar 145 kD antigen (p145) found in a wide range of human cancer cells.

A further object of the present invention is the provision of monoclonal antibodies specific to this common nucleolar antigen which can be used for diagnostic and treatment purposes.

A further object of the present invention is the provision of this nucleolar antigen in substantially purified form.

A further object of the present invention is the provision of processes for extracting and isolating the nucleolar antigen p145.

A further object of the present invention is the provision of diagnostic kits comprised of monoclonal antibodies specific to nucleolar antigen p145.

A further object of the present invention is the provision of monoclonal antibodies specific to the common nucleolar antigen p145 found in a wide range of human cancer cells which serve as carriers for markers for diagnostic purposes.

Other and further objects, features and advantages of the invention appear throughout.

DESCRIPTION OF THE PREFERRED EMBODIMENTS

The present invention resides in the unexpected and surprising discovery that a common specific nucleolar p145 antigen is present in the nucleoli of a wide range of human cancer cells, the extraction, isolation, and substantial purification, the production of monoclonal antibodies of high specificity and selectivity to this nucleolar antigen which can be tagged directly or indirectly to allow diagnostic testing for human cancers in vitro and in vivo.

The Antigen in the Cancer Cells

The antigen p145 has been found in a broad range of human cancers including cancers of the gastrointestinal tract, genitourinary tract, lung, liver, muscle, cartilidge, skin, and blood. For example, the malignant human cells include HeLa cells, prostatic carcinoma, other carcinomas, sarcomas, and hematological neoplasms. The antigen p145 can be extracted from nuclei or nucleoli of human malignant cells. The antigen has not been found in corresponding nontumor tissues.

The nucleolar antigen p145 is identified on one dimensional Western transfers by immunostaining with the specific monoclonal antibody as a single peptide band. The molecular size of the p145 antigen is approximately 145 kD based on Western transfer analysis using 6 to 8% SDS-polyacrylamide gels. Immunoelectron microscopy studies indicate that the antigen is localized diffusely throughout the nucleolus of cancer cells including the fibrillar centers where active transcription of rDNA occurs and in granular regions where preribosomal particles and assembled.

Nucleolar antigen p145 is extractable from human tumor nucleoli following homogenization in a 0.01M Tris buffer containing 0.2% deoxychlolate. Following centrifugation of this extract at 100,000 g, the antigen remains associated with nucleolar ribonucleoprotein (RNP) fraction. Antigen p145 is tightly bound to these particles but can be released following treatment with 4M guanidinium hydrochloride or RNAse. The p145 antigen has been purified to homogeneity by ion exchange and immunoaffinity chromatography or by 1 or 2 dimensional polyacrylamide gel electrophoresis.

It remains to be determined whether the antigen represents a substance that is present in high concentrations in cancer cells and very low concentrations in noncancerous cells or are fetal antigens as was found earlier in the comparative studies on nuclear antigens of the rat Novikoff hepatoma and normal rat liver cells (Yeoman et al., 1976).

Human Tumors and Other Tissues

All steps for obtaining and analyzing samples of human tissue, blood and serum of suspected cancer patients were approved by the Human Research Committee at Baylor College of Medicine, Houston, Tex. and affiliated hospitals. Sections of human tumors were obtained from frozen sections of surgical specimens, biopsy, or preserved cryostat specimens, mainly from the Department of Pathology from the Houston Veterans Administration Medical Center and also from The Methodist Hospital, Houston, Tex. These sections were analyzed for the presence of nucleolar antigens by indirect immunofluorescence and immunoperoxidase techniques.

Preparation of HeLa Cell Nucleoli

HeLa cells were collected from Spinner culture bottles (7–8 liters). The cells should be and were in log phase $7-8 \times 10^5$ cells/ml. The cells were centrifuged at $800 \times g$ for 8 minutes to form cell pellets. The cell pellets were suspended in (PBS) phosphate buffered saline (0.15M NaCl, 0.01M phosphate, pH 7.2) by gentle homogenization with a loose Teflon pestle and centrifuged at $800 \times g$ for 8 minutes. The cells were washed a second time with PBS and the cell pellets were weighed. The cell pellets were suspended by gentle homogenization in 20 volumes of recticulocyte standard buffer (RSB), pH 7.4 and allowed to swell for 30 minutes on ice. The cells were then centrifuged at $1000 \times g$ for 8 minutes and resuspended by gentle homogenization in RSB buffer plus 1/20 volume of the detergent Nonidet P40 (10% in RSB). The final volume of Nonidet was 0.5%. The cells were homogenized with a Dounce homogenizer 20–60 strokes until the cells were broken and the nuclei released and freed of cytoplasm. The cells were then centrifuged $1000 \times g$ for 8 minutes, resuspended by gentle homogenization in 0.88M sucrose, 0.5 mM Mg acetate ($20 \times$ weight-volume) and centrifuged at $1500 \times g$ for 20 minutes. The resulting pellet contained the HeLa nuclei that were used to prepare the nucleoli.

For isolation of nucleoli, the nuclear pellet as prepared above was next suspended by gentle homogenization in 0.34M sucrose, 0.5 mM Mg acetate using 2 ml of sucrose for each gram of original cells. The nuclei were sonicated (with a Branson sonifier) by 10-second bursts (and 10 seconds rest). Total time was between 60 and 110 seconds. The nucleoli released were monitored by microscopic examination. To visualize the nucleoli, they were stained with Azure C (the solution consists of 1% Azure C in 0.25M sucrose). The preparation should be free of nuclei at the end of the sonication period. The sonicated fraction was underlayed with three times the volume of 0.88M sucrose (without Mg acetate) and centrifuged $1500 \times g$ for 20 minutes. The resulting pellet contained the HeLa nucleoli which may be used as the immunogen.

Satisfactory purification has usually resulted with the above procedure (Busch and Smetana, 1970), and light microscopy showed the quality of these preparations was essentially satisfactory. The key problem in adequate purification of these preparations is the limited amount of original HeLa cells in the cultures which limit the number of repurification steps. Nucleoli prepared from 5- to 10-g HeLa cell preparations, rather than the 0.5- to 1-g quantities used in earlier studies, provided sufficient material for adequate purification. The conditions for growing the HeLa cells and the isolation of placental nuclei were essentially the same as those reported previously (Davis et al., 1979).

Preparation of the HeLa Nucleolar Extracts for Immunization

In some cases, nucleolar proteins were extracted from intact HeLa nucleoli and then subjected to salt fractionation to selectively remove immunodominant antigens shared by normal and tumorous tissue. For this purpose, the HeLa nucleoli were suspended in NaCl-EDTA buffer $10 \times$ weight/volume, 1 g nuclei/10 ml buffer. (Buffer: 0.075M NaCl, 0.025M Na EDTA/pH 8, 1 mM PMSF) The phenylmethylsulfonylfluoride (PMSF) is made up at 100 mM concentration in isopropyl alcohol. It is added to each solution prior to the extraction. The suspension was homogenized with a Dounce homogenizer 20 strokes and centrifuged at $3000 \times g$ for 5 minutes. Supernatant was collected. The above extractions were repeated on the nucleolar pellet a second time. The NaCl-EDTA extract was not used in the present antigen work; therefore, it was discarded. The nucleolar pellet was suspended in $10 \times$ weight/volume 0.01M Tris-HCl/20 mM dithiothreitol/0.2% deoxycholate/pH 8/1 mM PMSF and homogenized with a Dounce homogenizer for 20 strokes and allowed to set in an ice bath for 1 hr. The suspension was centrifuged at $3000 \times g$ for 15 min. The supernatant containing solubilized antigens was saved and the pellet was extracted two additional times as above. The supernatants were then combined and solid $(NH_4)_2SO_4$ was added to give a final concentration of 30% saturation. The mixture was allowed to precipitate for 3 hrs at 4° C. and then centrifuged at $3,000 \times g$ for 20 min. The supernatant containing the immunodominant nucleolar protein C23 was discarded and the precipitated nucleolar proteins lacking protein C23 was resolubilized in 1M NaCl-1M urea and used for injection.

A second approach for antigen preparation was the antibody masking of nontumorous antigens on tumor nucleoli. In this procedure, nucleoli purified from HeLa cells were spread by homogenization in low ionic strength buffer and by chelation of divalent cations. For each injection, nucleoli isolated from 5 g of HeLa cells were suspended in 0.01M Tris-HCl, pH 7.2, containing 5 mM EDTA and placed in an ice bath for 1 hr. Antinormal human liver antisera from 2 rabbits (10 ul of each antiserum) were added to the treated HeLa nucleoli and allowed to tumble overnight at 4° C. The resulting immune complexes were used for injection of 5 mice.

Immunization and Development of Monoclonal Antibodies

Female Balb/c mice were given 4 to 6 primary injections i.p. of either 200 ug of extracted nucleolar antigens devoid of C23 or of immune complexes as described above. The initial injection was given in incomplete Freund's adjuvant. One month after the last primary injection, mice were given a final series of injections over four consecutive days. The mice were injected each day with 400 ug of nucleolar extract or similar amounts of immune complexes in saline with injections given 50% i.v. and 50% i.p. On day five, the mice were sacrificed and spleen cells collected for fusion.

Cell Fusion and Cloning

Lymphocytes from mouse spleens were collected from a Ficoll-Hypaque gradient (M.A. Bioproducts, Walkersville, MD) and fused with P3-X63-Ag8.653 myeloma cells (Salk Institute, San Diego, CA). For each fusion, approximately $5 \times 10^7$ spleen lymphocytes were added to a 50 ml sterile conical tube containing $1 \times 10^7$ myeloma cells. The cells were mixed and washed once in serum free Dulbecco's modified Eagle's medium (DMEN, M.A. Bioproducts). The medium was removed and replaced with 1.0 ml of 50% polyethylene glycol (PEG) 1500 (M.A. Bioproducts) in DMEN. The PEG was mixed with the cells using a large bore pipet (10 ml) for one min and 7 ml of DMEN was added and allowed to set for 5 min. An additional 20 ml of medium was added and centrifuged for 15 min at 250 g. The washed cells were dispersed in 30 ml of DMEN supplemented with 20% fetal calf serum (AMF Biological and Diagnostic Products Co., Seguin, TX), a 2 mM L-glutamine, 1 mM pyruvate, 0.55 mM L-arginine, 0.27 mM L-asparagine, and 14 uM thymidine. The cell suspension was pipeted into 96-well microwell culture plates, 100 ul/well and incubated at 37° and 5% $CO_2$. An additional 100 ul of medium without aminopterin was added to the wells after one week. After 2 to 4 weeks of culture, the supernatants from wells containing growing cell clones were tested for nucleolar immunofluorescence on HeLa cells. Immunofluorescence positive wells were recloned by limiting dilution in 96 well plates containing approximately $10^5$ syngeneic spleen cells/well as feeder cells. Wells appearing to produce single colonies were retested for immunofluorescence and were recloned one additional time by limiting dilution. The recloned hybridomas were expanded to 24 well plates containing feeder cell layers and from there to flasks without feeder cells.

Growth of Hybridomas and Purification of Monoclonal Antibodies

To produce large amounts of antibody, hybridoma clones secreting antibody specific for nucleolar antigen p145 were grown as ascites tumors as follows. Approximately $5 \times 10^5$ hybridoma cells collected from cell culture were injected interperitoneally into mice that had been pretreated with pristine. After approximately one week of tumor growth, mice were tapped daily and ascites fluid collected and centrifuged to remove cells. Antibody was purified from ascites fluid by DEAE Affi-Gel Blue chromatography according to the method of Bruck et al., 1982. Purified monoclonal antibody was titrated for optimal immunofluorescence detection of antigen on control HeLa slides. The purified monoclonal antibody were aliquoted in PBS and stored at $-70°$ C. until used.

Hybridoma Deposit

Mouse hybridoma cell line NAP-145 has been deposited with American Type Culture Collection, 12301 Parklawn Drive, Rockville, Md. 20852, and accorded accession number HB 9562. Hybridoma NAP-145 is hybrid of mouse spleen cells fused with P3-X63-Ag8.653 myeloma cells. Hybridoma NAP-145 secrets monoclonal antibody having specificity against nucleolar antigens derived from HeLa cells and which antigens have a molecular weight of about $145,000 \pm 5,000$ daltons as measured by Western transfer analysis on polyacrylamide gel.

Immunofluorescence

The procedure described earlier (R. K. Busch, et al., 1974; Hilgers et al., 1972) for immunofluorescence was used in this study with a modification representing the introduction of a second antibody as a bridge.

Indirect Immunofluorescence method 50 ul of anti-p145 monoclonal antibody working solution was placed on acetone fixed HeLa cells or on fixed tissue specimens (from Hilgers et al., 1972; R. K. Busch et al., 1974). It may be necessary to use more than 50 ul if the tissue specimen covers a large section of the slide. Dilution of antibody is dependent on antibody concentration. Other dilutions can be used up to the point where Ab dilutions become too dilute to yield positive response to known positive cells (e.g. HeLa). The slides were incubated in a moist chamber for 45-50 minutes at 37° C. (The moist chamber may consists of a large petri dish to which has been added a moist paper towel.) After the incubation, the antibody solution was washed off the slide by the gentle addition of PBS and the slides were placed in a slide holder and washed in PBS for 1 hour. The PBS was changed three times, at 15 minutes, 30 minutes, and 45 minutes. The slides were removed from PBS and dipped in distilled or deionized water ten times with rapid up and down movements. A second unlabeled antibody (1:50 dilution of rabbit anti-mouse, Cappel) was then added as a bridge and incubated for 30 min at 37° C. The slides were washed as above and 50 ul of fluorescein labeled goat antirabbit antiserum (Hyland or Cappel) diluted 1:20 was placed on the slides and incubated in the moist chamber for 30-35 minutes at room temperature. The second antibody was removed from the slide by a gentle PBS wash. The slides were then washed in PBS for 1 hour with three changes, at 15 minutes, 30 minutes, and 45 minutes; or after the first 15 minutes wash, they can be placed in fresh PBS and left in the refrigerator overnight. After the final wash with PBS, the slides were dipped in deionized or distilled water ten times with rapid up and down movements and dried. A solution of 90% glycerol, 10% PBS, 4% n-propyl gallate, pH 8 was added to the cells or tissue specimen and covered with a cover slip. The specimen can be preserved for several months if the cover slip is sealed with a sealant, such as clear nail polish and kept cold. The slide was then examined with a fluorescence microscope. Nucleolar fluorescence was not observed with preimmune immunoglobulin or preimmune IgG fractions. The other immunological techniques used were the same as those used in earlier studies (Kendall, 1938; Lowry et al., 1951; Dale and Latner, 1969; Laurell, 1972; Wallace et al., 1974; Marashi et al., 1979). For analysis of nucleolar localization of immunofluorescence, samples were switched in and out of phase contrast illumination during fluorescence observation.

Immunoperoxidase Method

Instead of fluorescein-labeled goat antimouse antibodies, 50 ul of peroxidase labeled goat antimouse antibodies 1:10 or 1:20 dilution was added. Localized peroxidase activity was demonstrated by a number or redox dye systems for light or electron microscopic examination. Other enzymes can serve as labels for the indirect method and peroxidase and other enzymes can be used directly by labeling the primary antibody.

Prepare Karnofsky's incubation medium as follows: weigh out enough diaminobenzidine (Sigma) and suspend in 0.05M Tris-HCl, pH 7.6 so that the concentration is 0.5 mg/ml. Prepare a hydrogen peroxide solution of 0.02% (in the 0.05M Tris-HCl buffer). Mix the 0.5 mg/ml DAB and the 0.02% $H_2O_2$ in equal proportions a 1:1 ratio (this solution was freshly prepared each time it was used and was kept cold during the preparation). Add 200-300 ul of the DAB and $H_2O_2$ mixture to the slide and incubate for 30 minutes in a moist chamber at room temperature.

After this incubation, remove the DAB and $H_2O_2$ mixture by washing the slide with the 0.05M Tris HCl pH 7.6 buffer to which has been added 0.1M NaCl. The slides are given two 10 minutes washes in 0.05M Tris HCl pH 7.6, 0.1M NaCl. After completion of the processing, the slides are examined by light microscopy.

Preparation of HeLa Cell Slides for Immunofluorescence

A stock supply of fixed HeLa cells wsa prepared as follows: Actively growing cells from the HeLa culture bottle were removed and washed one time with PBS, pH 7.2. The cells were suspended so that there were at least $1.5 \times 10^6$ cells/ml. One drop of the HeLa cell suspension was placed on each washed slide (cleaned with detergent, rinsed with distilled or deionized water, cleaned with alcohol, rinsed and dried with heated air from hair dryer) and spread slightly and allowed to dry at room temperature (or in cold overnight). The dried cells were fixed by placing the slides at 4° C. in acetone for 12 minutes. The slides were numbered with a diamond point glass marking pencil. The slides were used as positive controls for immunofluorescence.

Malignant Tumors as Detected with the Test Antibody

The present studies confirm that nucleolar antigens are present in tumor cells but are not found in nontumor tissues. Initial studies demonstrated that, both in cell cultures in human tumors and in specimens from either autopsy or biopsy samples, bright nucleolar fluorescence was produced by the triple antibody technique (indirect immunofluorescence), and a corresponding result was not obtained with a series of nontumor tissues. It is of much interest that this broad array of malignant tumors of ectodermal, endodermal, and mesodermal origin exhibited the presence of a common nucleolar antigen (Table I).

TABLE I

Immunoreactivity[a] of Human Cancer Tissues or Cancer Cells with a Monoclonal Antibody to Nucleolar Antigen p145.

| Specimens | Number of Samples | Immunoreactivity |
|---|---|---|
| Solid Tumors | | |
| Adenocarcinomas: | | |
| Primary, colon | 4 | + |
| Metastatic, colon tumor | 3 | + |
| Hepatocarcinoma | 4 | + |
| Breast Cancer | 4 | + |
| Lymphoma | 6 | + |
| Leiomyosarcoma | 2 | + |
| Carcinomas: | | |
| Clear cell, ovarian | 1 | + |
| Metastatic, skin | 1 | + |
| Lung Cancer | 4 | + |
| Chondrosarcoma | 1 | + |
| HeLa cells | 1 | + |
| Prostate Cancer | 1 | + |
| Hep II cells | 1 | + |
| Leukemias: | | |
| ALL | 7 | + |
| AMML | 2 | + |
| AML | 2 | + |
| CML | 1 | + |
| HL60 (Cell line) | 1 | + |

[a]Immunoreactivity was determined by indirect immunofluorescence microscopy. Tissue sections or cells were fixed and permeabilized in acetone and reacted with the monoclonal antibody FB1. Following incubation with primary antibody, a second antibody rabbit anti-mouse IgG was used, after which a specific immunoreactivity was detected with a fluorescein conjugated anti-rabbit antibody.
[b]+ indicates that all specimens examined showed positive immunofluorescence.

EXAMPLE 1

Normal Tissues—In 42 nontumor tissues there was no nucleolar fluorescence following incubation of the monoclonal antibody to p145 with the various fixed cell preparations. It was of particular interest that neither the Malpighian layer of the skin, nor the cells of the bone marrow, nor the crypts of Lieberkuhn demonstrated positive immunofluorescence with this procedure. Moreover, the variety of nontumor tissues adjacent to the neoplasms were also negative; these include many tissues of varying types. A group of benign tumors evaluated, including thyroid and breast fibroadenomas, were also negative (Table II).

TABLE II

Immunoreactivity[a] of normal human tissues, hypertrophied tissues and benign tumors with a monoclonal antibody to nucleolar antigen p145.

| Specimens | Number of Samples | Immunoreactivity |
|---|---|---|
| Normal tissues: | | |
| Peripheral blood leukocytes | 2 | — |
| Purified lymphocytes | 2 | — |
| Leukocytes (viral lymphadenitis) | 3 | — |
| Lymph nodes (hypertrophied) | 2 | — |
| Fibroblasts | 1 | — |
| Liver | 5 | — |
| Spleen | 2 | — |
| Kidney | 2 | — |
| Gall bladder | 3 | — |
| Heart | 2 | — |
| Pancreas | 2 | — |
| Adrenal | 1 | — |
| Lung | 1 | — |
| Prostate (normal) | 3 | — |
| Prostate (hyptertrophied)* | 3 | + |
| Testes* | 2 | + |
| WI 38 Fetal Fibroblasts | 1 | + |
| Benign Tumors: | | |
| Breast fibroadenoma | 2 | — |
| Thyroid Adenoma | 2 | — |

[a]Immunoreactivity was determined by indirect immunofluorescence microscopy. Tissue sections or cells were fixed and permeabilized in acetone and reacted with the monoclonal antibody FB1. Following incubation with primary antibody, a second antibody rabbit anti-mouse IgG, was added after which specific immunoreactivity was detected with a fluorescein conjugated goat anti-rabbit antibody.
*Nucleolar immunofluorescence was detected in the immature spermatogonia of the testes (2 specimens) and in ductal regions of hypertrophied prostate (2 of 3 specimens).

EXAMPLE 2

Artifacts—In the ductal regions of prostate, there was a region of fluorescence in each cell which was non-nucleolar that appeared to represent nonspecific localization of the fluorescent antibody to concretions. In liver tissues, a nonspecific localization of the antibody appeared to occur in the form of the aggregates, possibly a nonspecific attachment of antibody to glycogen granules. In some tissues, which was negative for nucleolar fluorescence, small nonspecific immunofluorescent specks were generally distributed with no special localizing features with regard to cell morphology. The diameters of these very small nonspecific precipitates were 0.5 to 0.1 m as compared to the nucleolar diameters in the nuclei and nucleoli which were 4 to 6 m.

EXAMPLE 3

Fluorescence during Phases of the Cell Cycle—The nucleolar fluorescence was readily visualized in the interphase nucleoli. In metaphase, the nucleolar fluorescence was not seen as a distinct entity but was visible between the chromosomes and in the junctional area between the "nucleus" and the cytoplasm. Inasmuch as the nucleolus largely disappears during metaphase and rRNA synthesis ceases in late prophase, it was not visible as a distinct entity in such cells (Tan and Lerner, 1972). However, the finding that remnants of the immunofluorescent products persist throughout mitosis suggests that the nucleolar substructures (rather than the nucleolar products) contain the antigen that is persistent epigenetically.

EXAMPLE 4

Malignant Tumor Negatives—In the series of malignant tumors, negative regions were found in varying extents throughout the slides. In general, these correlated with either necrotic or abscessed portioins of the neoplasms. In tumor sections adjacent apparently normal tissue was negative for immunofluorescence staining.

EXAMPLE 5

Labeling—Direct immunochemical methods for the demonstration of the antibodies include labeling the primary antibody with one or more of the following labels: a radioisotope for autoradiography such as $^{125}I$, $^{131}I$, $^{14}C$, or $^{3}H$; a fluorescent dye such as fluorescein or tetramethyl rhodamine for fluorescence microscopy, an enzyme which produces a fluorescent or colored product for detection by fluorescence or light microscopy, or which produces an electron dense product for demonstration by electron microscopy; or an electron dense molecule such as ferritin, peroxidase or gold beads for direct or indirect electron microscopic visualization.

Indirect immunochemical methods include labelling the second antibody or other binding protein specific for the first antibody with a fluorescent dye, an electron dense compound, an enzyme which produces a product detectable by light, fluorescence or electron microscopic examination or a radioisotope detectable by autoradiography.

The indirect immunochemical methods for the visualization of the antibodies include application of hybrid primary or secondary antibodies or antibody fragments (F(ab')) wherein part of the hybrid antibody preparation is specific for the nucleolar antigens, (hybrid primary antibody) or for the primary antibody (hybrid second antibody), and part is specific for a label, such as those mentioned in the preceeding paragraph.

DIAGNOSTIC KITS

Labelled conjugated and nonconjugated antibodies may be packaged separately in phosphate buffered saline (PBS) or other buffered suspending agents for distribution. Suitable suspending agents include glycerin, heparin, or sucrose. Suitable buffers include barbital buffers, morpholine buffers, MOPS-3-(N-morpholino) propane sulfonic acid, hepes-N-2-hydroxyethylpiperazine-N-2-ethane sulfonic acid, Tris carbonate and the like.

The present invention, therefore, is well suited and adapted to attain the objects and ends and has the features mentioned as well as others inherent therein.

While presently preferred embodiments of the invention have been given for purposes of the disclosure, changes can be made therein within the spirit of the invention as defined by the scope of the appended claims.

What is claimed is:

1. A human cancer cell associated nucleolar antigen purified to homogeneity characterized by:
   solubility in 0.01M Tris HCl/0.2% deoxychlolate pH 8.0;
   a molecular weight of about 145,000±5,000 daltons as measured by Western transfer analysis on polyacrylamide gel;
   localization in nucleoli of human cancer cells and absence from nucleoli of normal cells; and
   sedimentation with ribonucleoprotein particles within the nucleolus.

2. The antigen of claim 1 which is primarily localized in the nucleoli of HeLa cells.

3. Antibody having binding specificity to nucleolar antigen p145, which nucleolar antigen is characterized by:
   a solubility in 0.01M Tris HCl/0.2% deoxychlolate pH 8.0;
   a molecular weight of about 145,000±5,000 daltons as measured by Western transfer analysis on polyacrylamide gel;
   localization in nucleoli of human cancer cells and absence from nucleoli of normal cells; and
   sedimentation with ribonucleoprotein particles within the nucleolus.

4. The antibody of claim 3 which is a monoclonal antibody.

5. The antibody of claim 3 which has been produced with nucleoli isolated from HeLa cells.

6. A continuous cell line which produces monoclonal antibody having binding specificity to nucleolar antigen p145, which nucleolar antigen is characterized by:
   solubility in 0.01M Tris HCl/0.2% deoxychlolate pH 8.0;
   a molecular weight of about 145,000±5,000 daltons as measured by Western transfer analysis on polyacrylamide gel;
   localization in nucleoli of human cancer cells and absence from nucleoli of normal cells; and
   sedimentation with ribonucleoprotein particles within the nucleolus.

7. A process for the immunological detection of cancer in a human tissue or cell specimen comprising:
   contacting the specimen with antibody characterized by binding specificity to nucleolar antigen p145 and detecting the localization of said antibody in the nucleoli of malignant cells but not normal cells of said specimen.

8. The process of claim 7 wherein the specimen is selected from the group consisting of gastrointestinal tract, genito-urinary tract, lung, liver, muscle, cartilage, skin and blood.

9. The human cancer cell associated nucleolar antigen of claim 1 which has binding specificity for a monoclonal antibody derived from ATCC hybridoma deposit HB 9562.

10. The monoclonal antibody of claim 4 which has specificity for the same nucleolar antigen as a monoclonal antibody produced by the ATCC hybridoma deposit HB 9562.

11. The monoclonal antibody of claim 4 which is produced by the ATCC hybridoma deposit HB 9562.

12. The continuous cell line of claim 6 which is cultured from cells of ATCC hybridoma deposit HB 9562.

13. A diagnostic kit for performing immunoassays for detecting the presence of nucleolar antigen p145 which comprises multiple containers wherein one of said containers has therein antibody characterized by binding specificity to nucleolar antigen p145.

14. The diagnostic kit of claim 13 wherein the antibody is antisera.

15. The diagnostic kit of claim 13 wherein the antibody is monoclonal antibody.

16. The diagnostic kit of claim 13 wherein the antibody is conjugated with a label.

* * * * *